United States Patent [19]
Sancoff et al.

[11] Patent Number: 5,700,245
[45] Date of Patent: Dec. 23, 1997

[54] APPARATUS FOR THE GENERATION OF GAS PRESSURE FOR CONTROLLED FLUID DELIVERY

[75] Inventors: Gregory E. Sancoff, Windham, N.H.; Mark C. Doyle, San Diego; Frederic P. Field, Solana Beach, both of Calif.

[73] Assignee: Winfield Medical, San Diego, Calif.

[21] Appl. No.: 501,948

[22] Filed: Jul. 13, 1995

[51] Int. Cl.⁶ .................................................. A61M 37/00
[52] U.S. Cl. .......................... 604/145; 604/140; 604/141; 222/399
[58] Field of Search ...................... 604/140, 141, 604/142, 143, 144, 145, 146, 147

[56] References Cited

U.S. PATENT DOCUMENTS

| | | |
|---|---|---|
| 524,377 | 8/1894 | Carr . |
| 754,037 | 3/1904 | Anderson . |
| 1,469,501 | 10/1923 | Dollin . |
| 1,731,767 | 10/1929 | Cramer . |
| 1,832,817 | 11/1931 | Pearsons . |
| 2,105,690 | 1/1938 | Greenblatt . |
| 2,312,381 | 3/1943 | Bickenheuser . |
| 2,381,749 | 8/1945 | Hull et al. . |
| 2,473,912 | 6/1949 | Schwinn . |
| 2,759,337 | 8/1956 | Katz . |
| 2,815,152 | 12/1957 | Mills . |
| 2,845,090 | 7/1958 | Rost . |
| 2,912,018 | 11/1959 | Leech . |
| 3,023,750 | 3/1962 | Baron . |
| 3,053,422 | 9/1962 | Tenison et al. . |
| 3,122,181 | 2/1964 | Hebenstreit et al. . |
| 3,146,169 | 8/1964 | Stephenson et al. . |
| 3,153,414 | 10/1964 | Beall et al. . |
| 3,175,558 | 3/1965 | Caillouette . |
| 3,178,075 | 4/1965 | Riedl et al. . |
| 3,217,947 | 11/1965 | Bauerlein . |
| 3,357,601 | 12/1967 | Crawford et al. . |
| 3,367,545 | 2/1968 | Cook . |
| 3,384,113 | 5/1968 | Pennisi . |
| 3,385,481 | 5/1968 | Frangos . |
| 3,405,845 | 10/1968 | Cook et al. . |
| 3,429,672 | 2/1969 | Young . |
| 3,468,308 | 9/1969 | Bierman . |
| 3,577,512 | 5/1971 | Shepherd et al. . |
| 3,585,982 | 6/1971 | Hollinshead . |
| 3,595,467 | 7/1971 | Goglio . |
| 3,667,652 | 6/1972 | Morane et al. . |
| 3,708,089 | 1/1973 | Holder . |
| 3,718,236 | 2/1973 | Reyner et al. . |
| 3,736,930 | 6/1973 | Georgi . |
| 3,756,556 | 9/1973 | Georgi . |
| 3,800,794 | 4/1974 | Georgi . |
| 3,804,077 | 4/1974 | Williams . |
| 3,840,009 | 10/1974 | Michaels . |
| 3,993,061 | 11/1976 | O'Leary . |
| 3,994,294 | 11/1976 | Knute . |
| 4,012,203 | 3/1977 | Rosiere . |
| 4,013,422 | 3/1977 | Spinner . |
| 4,037,598 | 7/1977 | Georgi . |
| 4,043,489 | 8/1977 | Buckman . |
| 4,067,332 | 1/1978 | O'Leary . |
| 4,080,967 | 3/1978 | O'Leary . |
| 4,137,913 | 2/1979 | Georgi . |
| 4,203,441 | 5/1980 | Theeuwes . |
| 4,235,236 | 11/1980 | Theeuwes . |

(List continued on next page.)

FOREIGN PATENT DOCUMENTS

| | | |
|---|---|---|
| 1270781 | 12/1972 | United Kingdom . |
| 9207612 | 5/1992 | WIPO . |
| 9325269 | 12/1993 | WIPO . |

*Primary Examiner*—Sam Rimell
*Assistant Examiner*—Robert V. Racunas
*Attorney, Agent, or Firm*—Knobbe, Martens Olson & Bear, LLP

[57] ABSTRACT

The present invention relates to apparatus and method for the controlled delivery of fluid. The apparatus comprises chemical reactants which combine to generate gas and create pressure to drive a fluid from a container. The reactants and the environment in which the reaction occurs are controlled, thereby causing the fluid to be delivered from the device at a predetermined flow rate.

43 Claims, 6 Drawing Sheets

U.S. PATENT DOCUMENTS

| | | |
|---|---|---|
| 4,331,728 | 5/1982 | Theeuwes . |
| 4,353,887 | 10/1982 | Hess . |
| 4,360,131 | 11/1982 | Reyner . |
| 4,373,341 | 2/1983 | Mahaffy . |
| 4,376,500 | 3/1983 | Banks et al. . |
| 4,379,453 | 4/1983 | Baron . |
| 4,382,965 | 5/1983 | Sandine . |
| 4,478,044 | 10/1984 | Magid . |
| 4,491,250 | 1/1985 | Liebermann . |
| 4,510,734 | 4/1985 | Banks et al. . |
| 4,511,355 | 4/1985 | Franetzki . |
| 4,513,884 | 4/1985 | Magid . |
| 4,518,103 | 5/1985 | Lim . |
| 4,553,685 | 11/1985 | Magid . |
| 4,567,948 | 2/1986 | Rozniecki . |
| 4,597,959 | 7/1986 | Barr . |
| 4,601,893 | 7/1986 | Cardinal . |
| 4,618,487 | 10/1986 | Dubois et al. . |
| 4,626,241 | 12/1986 | Campbell et al. . |
| 4,629,620 | 12/1986 | Lindahl et al. . |
| 4,646,946 | 3/1987 | Reyner . |
| 4,648,955 | 3/1987 | Maget . |
| 4,663,147 | 5/1987 | DePrince . |
| 4,673,392 | 6/1987 | Keime . |
| 4,678,661 | 7/1987 | Gergely et al. . |
| 4,679,706 | 7/1987 | Magid . |
| 4,687,423 | 8/1987 | Maget . |
| 4,687,660 | 8/1987 | Baker . |
| 4,734,092 | 3/1988 | Millerd . |
| 4,780,117 | 10/1988 | Lahey . |
| 4,785,972 | 11/1988 | LeFevre . |
| 4,802,343 | 2/1989 | Rudick et al. . |
| 4,816,262 | 3/1989 | McMullen . |
| 4,847,093 | 7/1989 | Ayer . |
| 4,869,402 | 9/1989 | Ash, Jr. . |
| 4,870,805 | 10/1989 | Morane . |
| 4,886,514 | 12/1989 | Maget . |
| 4,895,133 | 1/1990 | Collins et al. . |
| 4,896,794 | 1/1990 | Banks et al. . |
| 4,902,278 | 2/1990 | Maget . |
| 4,923,095 | 5/1990 | Dorfman et al. . |
| 4,969,874 | 11/1990 | Michel et al. . |
| 5,009,340 | 4/1991 | Morane . |
| 5,022,564 | 6/1991 | Reyner . |
| 5,035,230 | 7/1991 | Steidl et al. . |
| 5,053,012 | 10/1991 | Edwards . |
| 5,054,651 | 10/1991 | Morane . |
| 5,057,285 | 10/1991 | Belt . |
| 5,106,374 | 4/1992 | Apperson . |
| 5,137,186 | 8/1992 | Moran . |
| 5,333,763 | 8/1994 | Lane et al. . |
| 5,342,627 | 8/1994 | Chopra et al. . |
| 5,397,303 | 3/1995 | Sancoff et al. . |
| 5,398,850 | 3/1995 | Sancoff et al. . |
| 5,398,851 | 3/1995 | Sancoff et al. . |
| 5,553,741 | 9/1996 | Sancoff et al. ............ 604/145 X |

APPARATUS FOR THE GENERATION OF GAS PRESSURE FOR CONTROLLED FLUID DELIVERY

BACKGROUND OF THE INVENTION

1. Field of the Invention

The present invention relates to chemical reactants and compositions for the generation of a gas pressure to drive a fluid from an infusion pump.

2. Background of the Art

The controlled delivery of liquids, particularly those containing medications, to patients has received substantial attention in the medical arts. The concept of drug infusion is that a patient can be given medication by intravenous delivery over a given, relatively prolonged, time period. In this manner, the need for repeated injections is eliminated and there is a reduced risk of a development of drug sensitivities. Moreover, it is widely believed that sustained treatment with a drug is generally more effective than a single bolus treatment. Further, infusion pump type devices allow for ambulatory treatment of a patient; i.e., the patient need not be attached to an intravenous ("IV") stand and bag.

There have been a number of products in the past which have been useful for delivering liquids, including medications, at a controlled flow rate. Some of these include infusion pumps which use gas pressure to administer an infusion liquid into a patient. For example, in Baron, U.S. Pat. No. 4,379,453, an infusion bag is equipped with an internal bag including a set of reactive chemicals that, when mixed, react to form a gas that inflates the internal bag to drive a liquid from the infusion bag. Similarly, in Baron, U.S. Pat. No. 4,379,453 the inventor disposed the reactive chemicals into a cuff-like apparatus to squeeze the liquid from the infusion bag.

The use of gas pressure, without the need for a chemical reaction, has also been demonstrated. See U.S. Pat. No. 5,106,374.

However, in each of the above-described patents, there is a limited ability for an operator to control the pressure of the gas and ultimately the flow rate of the liquid from the device. Baron, in U.S. Pat. No. 4,379,453, attempted to solve this problem by utilizing a plurality of reactions. However, this system merely creates two "peaks" in pressure and consequently flow rate.

Moreover, many of the prior art devices are only effective in a particular orientation. When gas is generated in one location in a system involving a liquid reactant, and the gas is used in a different location, it is desirable that only the gas (i.e., not the liquid reactant) leave the site of generation. Furthermore, it is desirable that the infusion device be operable in any orientation, so that it can be tipped and moved during use by an ambulatory patient, without affecting the operation or location of the reactants.

Accordingly, a need exists in the art for infusion devices which deliver fluids in a controlled manner.

SUMMARY OF THE INVENTION

The present invention solves the foregoing problem in the art through the provision of particular chemical reactants and compositions of the chemical reactants that allow for the controlled generation and pressure of a gas in, and consequently the flow rate of a liquid from, an infusion pump. The present invention allows for the retention of liquids such as medications in usable form over an extended shelf life without leakage or loss of the ability to be rapidly and thoroughly dispensed, and which can be activated for dispensing quickly and without the need for additional equipment, such as pressurized gas cylinders, to effect the activation. Unlike the delivery systems of the prior art, which had to be activated initially and then suffer short shelf life, or which required complicated and time consuming methods of subsequent activation, the present invention remains inert and ready for use for long periods and then can be quickly and easily activated when needed, to deliver the medication in a controlled, consistent manner.

Furthermore, the device can be used in any orientation, and reactants can be maintained in one location while the gas reaction product is directed, as a working fluid, to another location.

DETAILED DESCRIPTION OF PREFERRED EMBODIMENTS

In accordance with the present invention, there are provided chemical reactants and compositions of the chemical reactants to ensure the controlled generation of a gas from a gas generating reaction in order to provide a substantially constant pressure and consequent controlled flow rate of a liquid from an infusion pump. In general, infusion pumps in which the present invention is particularly useful include a housing divided into a liquid reservoir and a gas expansion reservoir with a membrane or other flexible divider disposed therebetween. The membrane ordinarily extends substantially into the gas expansion reservoir when the pump is filled with a liquid contained in the liquid reservoir. When gas expands within the gas expansion reservoir, the membrane is forced into the liquid reservoir, displacing liquid. In a preferred embodiment, the gas expansion reservoir is in communication with a gas generating chamber. The gas generating chamber separately houses the reactive chemicals which produce the gas.

As will be appreciated, the control aspects of the present invention are equally applicable with respect to other infusion pump designs and would be expected to operate more effectively than previous designs.

The present invention involves the use of a controlled chemical reaction that evolves gas. The reaction is started by an operator of the infusion apparatus when needed. The reaction occurs in a container and the gas generated by the reaction operates to apply pressure on a liquid separated from the gas evolution reaction. The pressure exerted on the liquid forces the liquid out of a port at a flow rate that is determined by means of a restriction in the liquid delivery set.

Chemical Reactants:

Various chemical reactants can be used effectively to generate a gas which is then used to drive fluid from an infusion pump. Preferably, the gas generated is carbon dioxide. Carbon dioxide is generally quite inert and safe at low concentrations. However, other gases could also be used, provided they are relatively inert and safe.

In order to generate carbon dioxide, two or more reactive chemicals are mixed that upon reaction generate a gas. Preferably, one of the reactants is provided in liquid form, i.e., a liquid chemical, a solution, or the like, and another one of the reactants is provided as a solid. Either the liquid or the solid may comprise more than one reactive chemical. However, for simplicity, each of the liquid and the solid preferably contain only one reactive species.

For the purposes of the following discussion, it will be assumed that carbon dioxide is to be generated. As mentioned above, to generate the gas, at least two reactants are caused to come into contact. For ease of reference, the reactants will be referred to herein as a first reactant and a second reactant or a solid reactant and a liquid reactant and, particular sets of reactants will be referred to as reactant sets.

First Reactant:

Preferably, the first reactant is selected from the group consisting of carbonates and bicarbonates, particularly, Group I and II metal carbonates and bicarbonates (the "carbonate"). For example, preferred carbonates include sodium bicarbonate, sodium carbonate, magnesium carbonate, and calcium carbonate. However, sodium bicarbonate, sodium carbonate and calcium carbonate are highly preferred, with sodium carbonate (or soda ash) being the most highly preferred. A desirable feature of sodium carbonate is that it is easily sterilizable. For example, sodium carbonate can be sterilized with heat, such as through autoclaving. This is preferable, since the infusion devices for use with the invention are designed for human use and it is safer to ensure that all of the components are sterile whether it is expected that they will come into contact with the patient or not. Other reactants that are sterilizable with heat are equally useful.

The carbonate can be either used as a solid reactant or can be dissolved in a solution to form a liquid reactant. In a preferred embodiment, the carbonate is used as a solid. The reason for this choice is that the carbonates are all solids and some are only sparingly soluble in water.

Second Reactant:

The second reactant is preferably an acid. Preferably, the acid is selected from the group consisting of acids, acid anhydrides, and acid salts. Preferably, the second reactive chemical is an organic acid such as citric acid, acetic acid, or acetic anhydride, or sodium bisulfate.

Usually the second reactant is used as the liquid reactant. However, in the case of citric acid and sodium bisulfate, for example, the second reactant can also be the solid reactant. Nevertheless, generally the second reactant is more soluble in water than the first reactant and is, therefore, used to form the liquid reactant.

Reactant Sets:

A reactant set is based upon a variety of considerations. For example, the solubility of the first and second reactants are considered to determine which reactant should be used as the solid or liquid reactant. Also considered is the product of the reaction and its solubility. It is preferred that the products be carbon dioxide ($CO_2$) gas and a soluble inert compound. Once these factors are considered, appropriate reactant sets can be constructed. For instance, as will be appreciated, in preferred embodiments, reaction sets such as those shown in Table I may advantageously be employed:

TABLE I

| Solid Reactant | Liquid Reactant |
| --- | --- |
| Sodium Carbonate | Citric Acid |
| Calcium Carbonate | Acetic Acid |
| Magnesium Carbonate | Citric Acid |

Once the appropriate reactant sets are established, it is important to determine the operating parameters that will be necessary to control the generation of the gas and, therefore, provide a substantially constant flow rate. As will be appreciated, the mere reaction of the solid reactant as a powder and the liquid reactant in the above reactant sets in the atmosphere at standard temperature and pressure will liberate gas at the maximum kinetic rate for the reaction.

When enclosed under some pressure and under a $CO_2$ atmosphere, the kinetics will be slowed. Nevertheless, a flow rate of a liquid driven from a pump by the gas, upon reaction of the first and second reactants without any other control, will not be substantially constant. Rather, the flow will initiate, increase rapidly, level off, and then subside.

Accordingly, we discovered that through the introduction of certain control parameters, the rate of generation of a gas can be controlled, allowing the pressure of the device to be maintained constant and thus the flow rate from the infusion pump can be maintained at a substantially constant rate. The control parameters include the structure or geometry of the solid reactant, the composition of the solid reactant, solid reactant surface modifications, the viscosity of the liquid phase, and the environment in which the gas generating reaction occurs.

Configuration of the Gas Generating Chamber

The present invention provides for various configurations of fluid delivery systems. Such systems include a gas generating chamber wherein gas is generated and used to deliver fluid from an infusion pump. The reaction rate of the chemicals which generate the gas can be tailored to meet a user's specific requirements. Through arranging or allowing contact of the chemicals in a predetermined manner, and controlling the pressure of the gas, a gas generation and pressure profile can be generated. This gas generation and pressure profile can, for example, start at an initial profile designed to deliver fluid from the pump at an initial slow rate and can, thereafter, increase, to deliver fluid at a second increased rate. This is advantageous in certain applications, such as delivery of cancer chemotherapeutic agents. Multiple stages of fluid delivery can be implemented through predetermination of a desired pressure and gas generation profile and design of the chemical reactants or their contact to achieve that profile.

In a preferred embodiment, the composition of the solid reactant is modified by coating granules of the solid reactant with a soluble compound which acts to delay the entry of the liquid reactant. The granules can be coated with different thicknesses of coating, or alternatively, different types of coatings may be used. Through the use of a coating on granules of the solid reactant, the contact between the liquid and solid reactants can be varied, resulting in a sustained generation of gas over an extended period of time. In a particularly preferred embodiment, a first group of particles is uncoated, a second is coated with a relatively short duration coating, a third is coated with a coating that delays entry of the liquid reactant for a longer time, and so forth.

Exemplary materials that are useful as surface treatments include ethylcellulose (AQUACOAT, available from FMC Corporation), plasticized ethylcellulose (SURELEASE, available from Colorcon) and acrylic polymers (EUDRAGIT, available from Rohn Tech Inc.). These materials can be used with success to delay the reaction between the solid and liquid reactants and achieve the generation of gas over an extended period of time.

In the fluid delivery system of the present invention, the rate at which the liquid reactant contacts the solid reactant is controlled. A porous material is used to absorb the liquid reactant and deliver the liquid to the solid reactant in such a way as to contact only a portion of the solid reactant at any given time. This allows for the continuous generation of gas over time. By controlling the porousness and the amount of material used to absorb the liquid reactant, control over the rate at which the gas is generated can be obtained.

In one preferred embodiment of the present invention, the porous material is a sponge. The solid reactant is in the form of granules or powder imbedded in the sponge. The sponge is sized so as to absorb all of the liquid reactant, which acts to keep the liquid reactant in contact with the solid reactant, and also keeps the liquid reactant from spilling out of the gas generating chamber. As the sponge absorbs the liquid reactant, the liquid is brought into contact with the solid reactant in the sponge and gas is generated. Use of particles of different sizes and/or particles with a range of time delay coatings can flatten the curve relating gas generation to elapsed time.

In an alternate preferred embodiment, the porous material is in the form of a wick. As the liquid reactant is brought into contact with the wick, the wick absorbs the liquid and through a wicking action, the liquid is carried along the length of the wick, contacting the solid reactant. The solid reactant can be in the form of granules or powder imbedded in the wick along its length, or alternatively, can be a solid block or tablet which lies along the outside length of the wick. The solid tablet can also be formed of numerous small granules packed into tablet form. Suitable wicking materials include natural and synthetic hydrophilic polymers, including cellulosic and lignocellulosic materials such as blotting paper, cotton or other vegetable fiber; and synthetic polymers such as woven polypropylene fiber, polyester fiber, polystyrene fiber, and polyamide fiber.

In the preferred embodiment having the solid reactant in the form of a block or tablet, the tablet is formed using a tablet or pill press. The tablet is comprised of the solid chemical reactant mixed with a filler. The filler acts to slow the dissolution of the solid reactant. Essentially, the filler acts to "dilute" the amount of the solid reactant in reactive contact with the liquid reactant at any one time, and/or to create a viscous boundary layer which slows the mixing of reactants and removal of products. These rate controlling fillers or binders can be added to the solid reactant at varying concentrations. Fillers or binders are quite effective to slow the reaction rate or limit the access of the liquid reactant to the solid reactant. Examples of suitable fillers or binders include polyvinylpyrrolidone (i.e., PLASDONE, available from ISP Technologies, Inc., Wayne, N.J.), polyethylene glycol (i.e., PEG 400 available from Olin Corp., Stamford, Conn.), and polyvinyl alcohol (i.e., PVA 205S available from Air Products, Allentown, Pa.), AC-DI-SOL Croscarmellose Sodium (cross-linked sodium carboxymethylcellulose) (available from FMC Corporation, Philadelphia, Pa.). Similarly, there are a large number of excipients or carriers that will act to slow the chemical reaction.

Alternatively, as will be appreciated, it is possible to vary the concentration of the liquid reactant in order to modify the reaction rate with the solid reactant. It is also possible to add viscosifiers to the liquid reactant to slow the mixing rate of the reactants and the rate at which the gaseous product moves away from the reactants.

In the system of the present invention, the solid and liquid reactants are initially separated through the use of an openable barrier. This barrier can be in the form of a frangible barrier such as thin foil, plastic or glass. When the barrier is ruptured, the liquid and solid reactant are brought into contact. Alternatively, the openable barrier is a valve. When the valve is opened, the liquid reactant passes through it and contacts the solid reactant. It will be appreciated that any form of barrier which acts to initially separate the solid and liquid reactants, but allows the reactants to contact one another upon operation of the device, can be used.

Various preferred embodiments of the present invention will now be described in detail.

Sponge/Granule System

Figure 1:
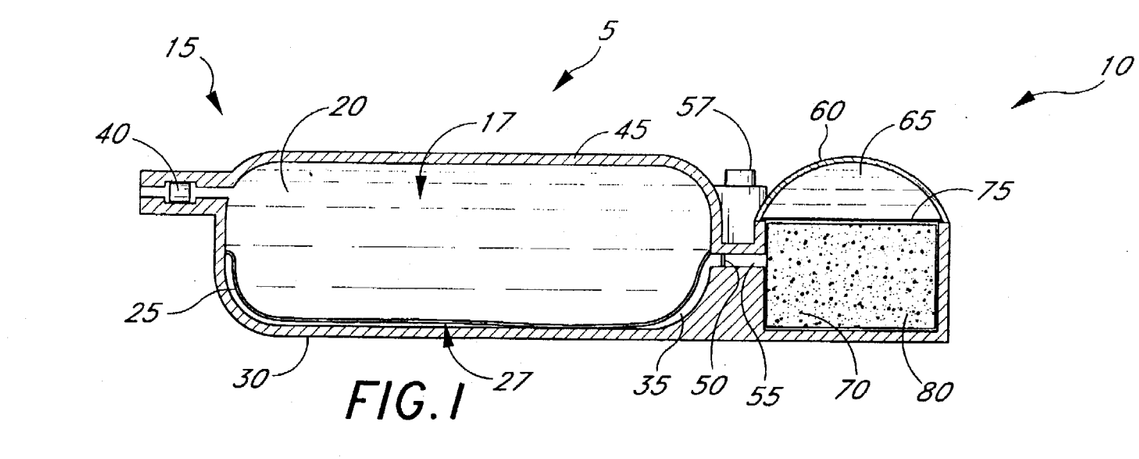
FIG. 1 is a cross-sectional side view of an infusion pump having a fluid delivery system in accordance with the present invention comprising a sponge having granules of solid reactant imbedded therein.
Figure 2:
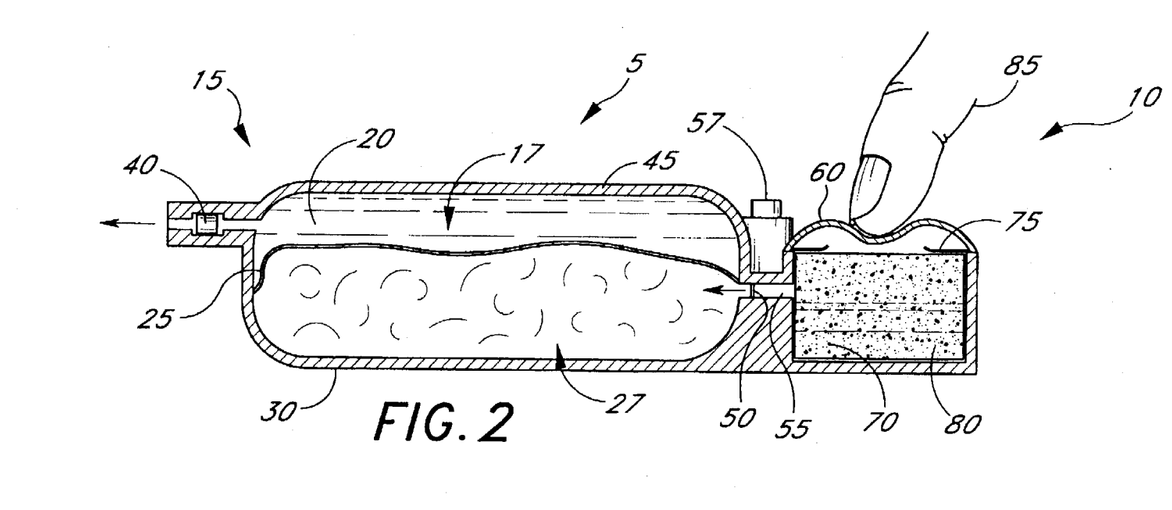
FIG. 2 is a cross-sectional side view of the device of FIG. 1 showing its mode of operation.
Figure 9:
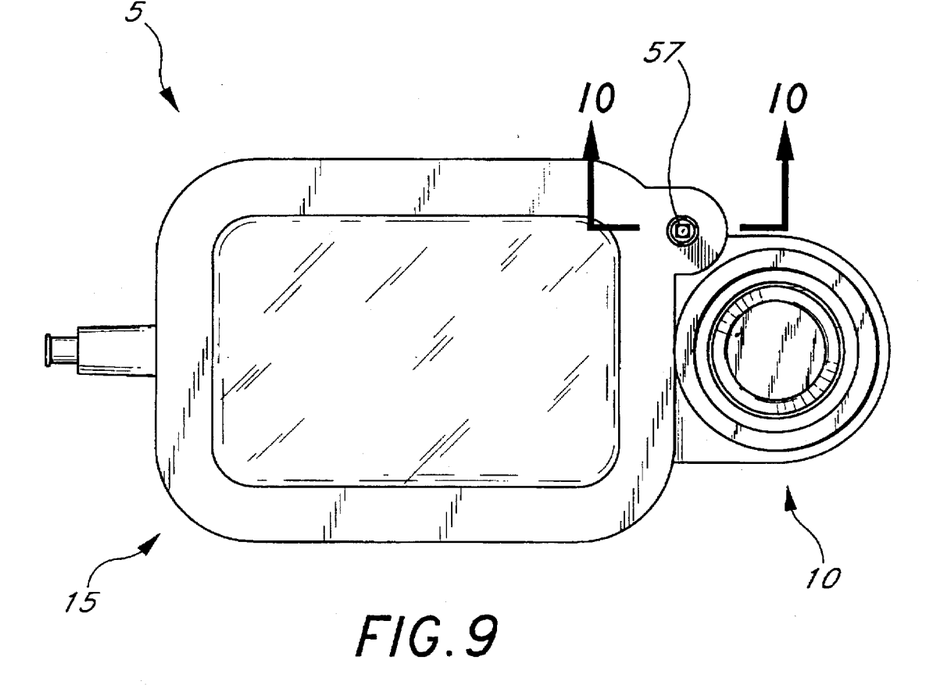
FIG. 9 is a top view of the device of the present invention.

A preferred embodiment of the present invention is illustrated in FIGS. 1, 2 and 9. An infusion device 5 having a separate gas generating chamber 10 according to the present invention is shown in FIGS. 1 and 9. The device 5 is advantageously of a rectangular shape with rounded edges. It is divided into two separate compartments: a fluid delivery compartment 15 and a gas generating compartment 10. The fluid delivery compartment 15 contains a flexible membrane 25, which divides the compartment 15 into a liquid reservoir 17 and a gas expansion reservoir 27. The flexible membrane 25 is held in proximity to, or distended towards, an outer wall 30 in the lower section of the fluid delivery compartment 15 by liquid 20. The flexible membrane 25 may contact the outer wall 30, or there may be a slight space 35 between the outer surface of the flexible membrane 25 and the inner surface of the wall 30. The liquid reservoir contains or is adapted to contain a liquid 20, such as a liquid medication, that is to be delivered to a patient.

Preferably, the liquid 20 is additionally kept within the fluid delivery compartment 15, by a one-way valve 40. The valve 40 can be specially manufactured or can be a standard one-way luer fitting, such as those that are commercially available. For example, the Halkey-Roberts Corporation (St. Petersburg, Fla.) produces a variety of luer syringe check valves that can be used for this purpose. We prefer to use Halkey-Roberts Model No. V24200.

It is preferred that all materials that are in contact with the liquid 20 in the fluid delivery compartment 15, such as the flexible membrane 25, the wall 45, and the valve 40 and its components be constructed of materials that are non-leaching and are appropriate for medical use. One example of such a material is ultrapure polypropylene and other similar materials. In U.S. Pat. No. 4,803,102 one formulation of ultrapure polypropylene is described. Thinner preparations of ultrapure polypropylene (i.e., 0.002 to 0.010 inch gauge) are used in preparing the flexible membrane 25 and thicker gauge materials (i.e., molded to 0.030 to 0.060 inch gauge) are preferred for making the case of the device which is defined by walls 30 and 45. The case of the device can be rigid to provide added structural support, or alternatively, can be flexible. The flexible casing is preferably formed from sheets of polypropylene film.

Further, the flexible membrane 25 is preferably constructed to be gas impermeable, i.e., impermeable to the gas that is generated in the reaction between the solid reactant 70 and the liquid reactant 65 described above. In order to attain gas impermeability in the membrane 25, either a gas impermeable material, such as polyvinylindene dichloride, polyethylene terephthalate, or polyether terephthalate can be used or a composite membrane or bi- or multi-layer membrane can be prepared. For example, the surface of the flexible membrane 25 in contact with the liquid 20 in the fluid delivery compartment 15 can be prepared from ultrapure polypropylene, as described above, while the surface in contact with the gas generated by solid and liquid reactants can be prepared from polyvinylindene dichloride or polyether terephthalate.

As illustrated in FIG. 1, the gas generating chamber 10 preferably is in fluid communication with the gas expansion reservoir 27 through a channel 50. Thus, as gas is generated in the gas generating chamber 10 it will travel through the channel 50 and into the gas expansion reservoir 27.

The gas generating chamber 10 of the present invention additionally comprises a depressible membrane 60 which is sealingly joined to the case of the device 5. The depressible membrane 60 sits above the gas generating chamber 10. Inside the gas generating chamber 10 are the reactants for generating gas. Shown in this embodiment is a liquid reactant 65 that is separated from the solid reactant 70 by an openable barrier 75 comprised of material such as thin foil, which ruptures when pressure is applied to the depressible membrane 60.

In the highly preferred embodiment illustrated in FIG. 1, the liquid reactant 65 is an aqueous solution of citric acid, preferably at a concentration of about 33% by weight citric acid, and at an exemplary volume of about 12 ml. The solid reactant 70 is in the form of small granules of sodium carbonate. The granules 70 are shown imbedded in a natural or synthetic sponge 80 (which may be any porous or absorbent hydrophilic solid). The granules of solid reactant 70 are preferably coated with a soluble compound which serves to delay the entry of the liquid reactant 65, and thus delay the gas generating reaction between the two reactants. The granules 70 are coated with different thicknesses, or alternatively, different types of coating, which causes the granules 70 to be consumed at different times. Alternatively, the granules are of different sizes, or have differing amounts of binder. Any of these alternatives may be used to sustain the reaction between the solid 70 and liquid 65 reactants over a predetermined period of time.

As described above, the granules 70 are imbedded in a sponge 80, which is wetted by the liquid reactant 65 when the reaction is initiated. The liquid reactant 65 disperses evenly within the sponge 80, preferably wetting all of the granules 70 at about the same time. The granules 70 then react with the liquid 65 according to the thickness or type of coating on the granule 70. The size of the granules 70 is such that the reaction product does not grow to the point of preventing the granules 70 from efficiently contacting the liquid reactant 65 (a size that may be determined empirically without undue experimentation for any sponge/granule/liquid reactant system). Additionally, the sponge 80 is preferably sized so as to contain all the liquid reactant 65, thus maintaining the liquid in the reaction chamber while permitting generated gas to leave, regardless of the orientation of the device during gas generation.

The coating on the surface of the granules 70 serves to temporarily limit the exposure of the solid reactant to the liquid reactant 65. By varying the solubility of the coating on the granules 70, for example by varying the thickness or content of the coating, the gas generating reaction can be extended over a period of time. Accordingly, control is achieved over the gas generation profile and correspondingly the flow rate profile of the infusion pump.

As will be understood, the use of a sponge 80 containing the solid reactant 70 which absorbs the liquid reactant 65 is very useful in that it retains the reactants within the gas generating chamber 10. This reduces concerns that the reactants could mix with the liquid 20 in the fluid delivery compartment 15. An additional advantage to the use of a sponge 80 with the granules of solid reactant 70 imbedded therein is that it enables the device 5 to be used in any orientation. The reactants in the gas generating chamber 10 remain physically separated from the fluid delivery compartment 15 and the liquid 20 therein, and regardless of the orientation of the device, gas will continue to be delivered to the gas expansion reservoir 27 in the fluid delivery compartment 15. This makes the device 5 very versatile. For example, medical personnel do not have to carefully orient the device 5 and ambulatory patients can carry the device 5 in their pockets.

It will be appreciated that the advantages associated with the fluid delivery system of the present invention, such as allowing the orientation of the device to be an insubstantial consideration since the chemical reactants will not get near the fluid to be delivered to the patient, and allowing the chemical reactants to stay in contact with one another so as to continue the chemical reaction therebetween, can be achieved through a number of other mechanisms. In general, therefore, any mechanism that allows the gas generated by the reaction between the reactants to be communicated to the pump while the chemical reactants remain in contact away from the pump can be used.

Turning now to FIG. 2, the operation of the first embodiment of the infusion device 5 of the present invention will be described. To begin the gas generating reaction, the user depresses the depressible membrane 60 with their finger 85, as illustrated in FIG. 2. The pressure caused by this action causes the openable barrier 75 separating the solid 70 and liquid 65 reactants to rupture. The liquid citric acid 65 then soaks into the sponge 80, contacting the sodium carbonate granules 65 and generating carbon dioxide.

Carbon dioxide gas will flow through the channel 50 and into the gas expansion reservoir 27. As the gas pressure builds against the flexible membrane 25, pressure is transferred to the liquid 20 inside the fluid delivery compartment 15. Thereafter, provided that the valve 40 is opened, liquid 20 will begin to flow through the valve 40.

Figure 10:
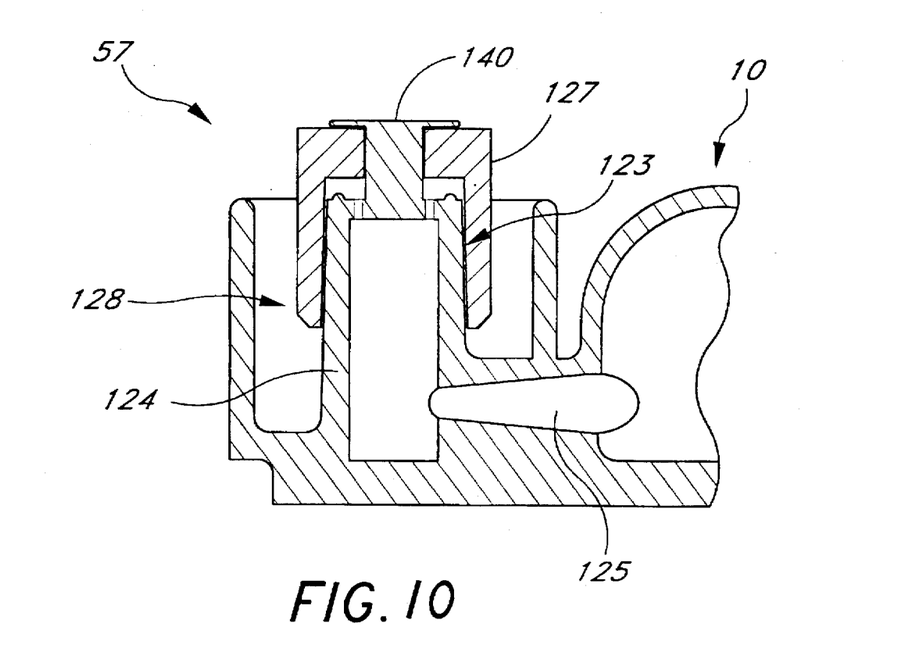
FIG. 10 is a side view of a relief valve designed for use with the device of the present invention, taken along line 10—10 in FIG. 9.

As an additional control feature and for safety, most infusion pumps with which the fluid delivery system of the present invention is designed to work include a pressure relief valve. A simple but highly effective relief valve is illustrated in FIG. 10. The pressure relief valve 57 is in communication with the gas generating chamber 10 through a gas channel. An elastomeric valve 127 can be seated on a stud 140 which is located at the top of a tapered valve stem 124. The valve 127 has an opening through which the stud 140 traverses. The valve 127 is preferably cylindrically shaped and extends past the stud 140 to surround the valve stem 124, which extends into a receiving channel 128 in the valve 127. Gas channels 123 are located between the stud 140 and the tapered, cylindrical valve stem 124. The valve 127 is seated on the stem 124 such that when the pressure exceeds a desired level, gas escapes out from underneath the valve 127 and through the open gas channels 123. In operation, when gas pressure in the device exceeds a selected pressure level, the valve 127 is deformed so as to define open gas channels 123 which create a gas flow path through which excess gas flows to the outside of the device. This reduces excess gas pressure in the device, and prevents overpressurization when fluid flow out of the device is stopped and also serves to maintain the pressure of the device at a predetermined set point. While the system operates at preferably 10 psi or less, when the system exceeds 10 psi, the gas will be forced out the pressure relief valve, allowing gas to escape from the device 5.

The position of the valve 127 on the tapered stem 124 produces more or less pressure between the outer valve stem wall and the inner arms of the valve 127. This determines the interference between the valve 127 and the stem 124. Valves of varying stiffness or diameter can be calibrated by moving them to a position on the stem 124 which results in release of gas from the system at the desired pressure. Once the valve 127 has been positioned on the stem 124 in the desired location, the end of the stud 140 is swaged down to prevent the valve 127 from moving off the stem 124 and changing the calibration.

We have discovered that use of the pressure relief valve in combination with the choice of reactants, porous material and coating of the granules, we can achieve an almost completely linear pressure profile. Such a linear pressure profile gives rise to an almost perfectly linear flow rate of liquid from the pump.

Wick System

Figure 3:
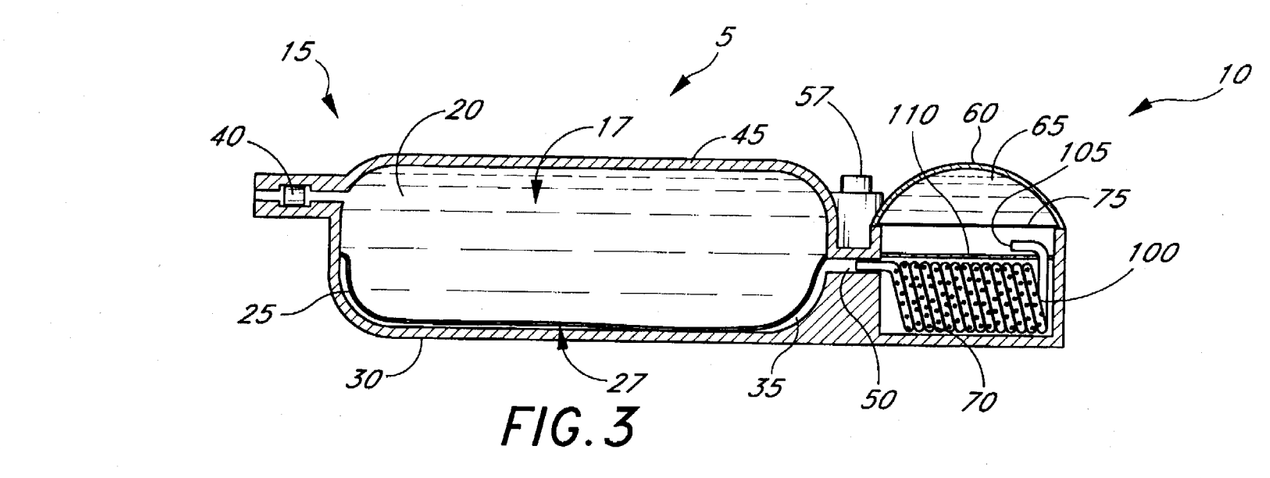
FIG. 3 is a cross-sectional side view of an infusion pump having an alternative embodiment of a fluid delivery system in accordance with the present invention comprising a wick having granules of solid reactant imbedded therein.
Figure 4:
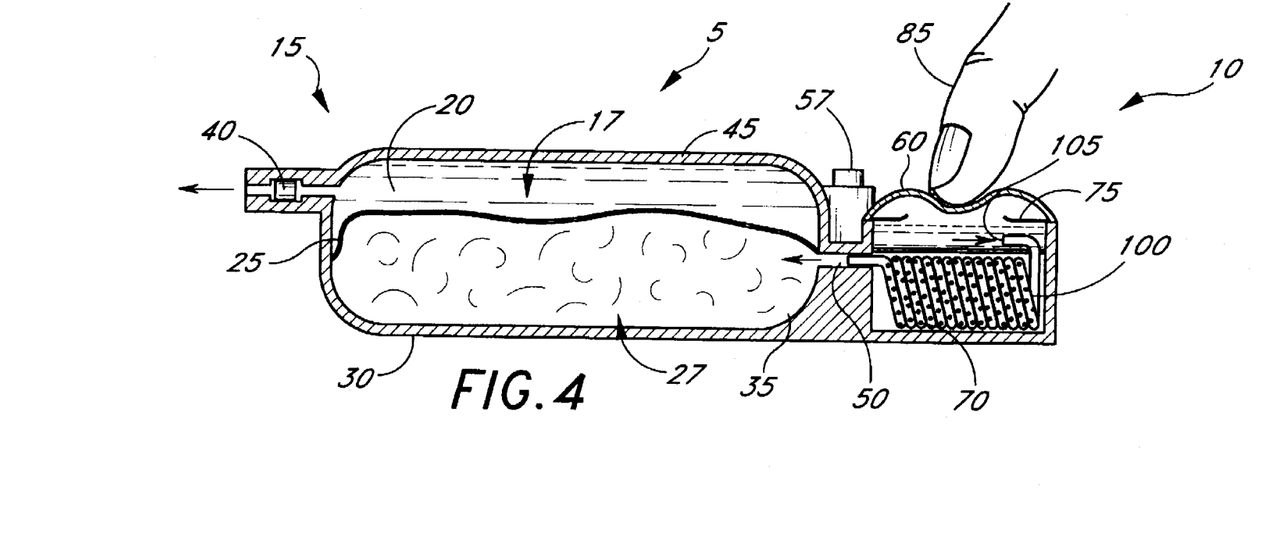
FIG. 4 is a cross-sectional side view of the device of FIG. 3 showing its mode of operation.

In another preferred embodiment of the present invention, illustrated in FIGS. 3 and 4, the porous material comprises a wick 100. The opening of the wick 105 is separated from the length of the wick 100 by an insoluble barrier 110. The granules of solid reactant 70 are imbedded in the wick 100, and are optionally coated with a time release coating as described above in connection with FIGS. 1 and 2. Pressure on the depressible membrane 60 ruptures the openable barrier 75, bringing the liquid reactant 65 into contact with the opening of the wick 105, which lies above and is separated from the rest of the wick 100 by the barrier 110. The liquid reactant 65 enters the opening of the wick 105 and travels along the length of the wick 100 at a predetermined rate which is established by the nature of the wick material. As the liquid reactant 65 contacts the solid reactant 70, gas is produced by the resulting reaction and travels out of the wick 100 in the direction opposite the flow of the liquid 65, and into the gas expansion reservoir 27. Preferably, the wick 100 is long enough to hold all of the liquid reactant 65. By varying the length of the wick 100 and the rate at which the wick 100 absorbs the liquid reactant 65, as well as the coating or concentration of the granules 70, the desired flow rate of fluid from the pump can be achieved.

Figure 5:
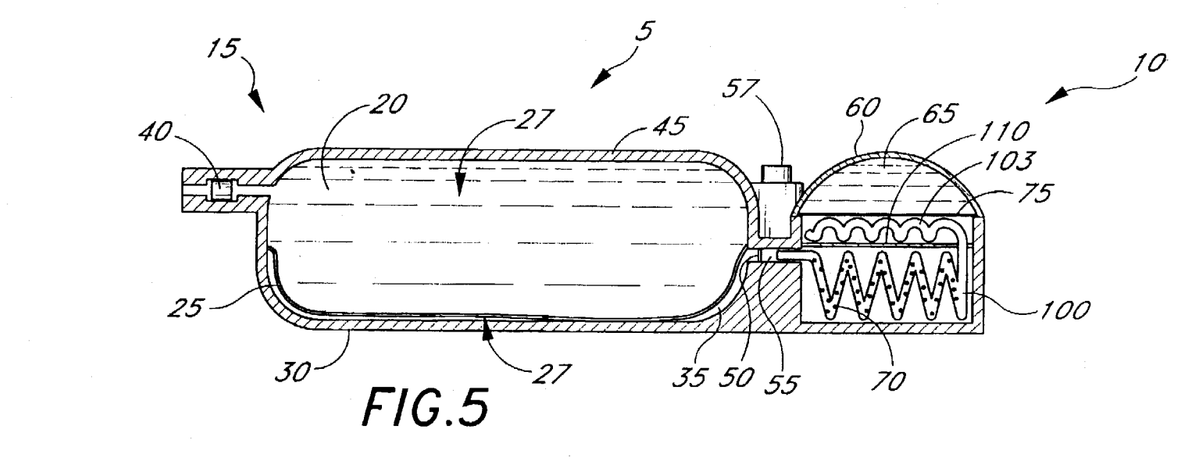
FIG. 5 is a cross-sectional side view of an infusion pump having an alternative embodiment of a fluid delivery system in accordance with the present invention comprising a wick having granules of solid reactant imbedded in the lower portion of the wick, the upper portion of the wick being sized so as to absorb substantially all of the liquid reactant.
Figure 6:
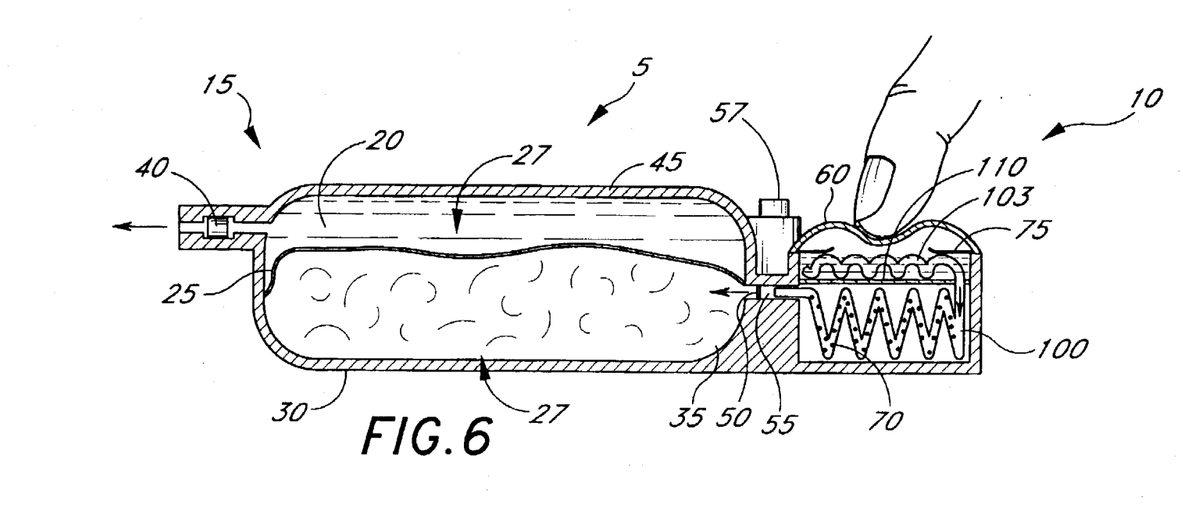
FIG. 6 is a cross-sectional side view of the device of FIG. 5 showing its mode of operation.

In another preferred embodiment of the present invention, illustrated in FIGS. 5 and 6, a portion of the wick 103 sufficient to absorb all the liquid reactant 65 upon opening of the openable barrier 75 lies above and is separated from the rest of the wick 100 by the insoluble barrier 110. The upper portion of the wick 103 is not in contact with the solid reactant 70. The liquid reactant 65 is transported along the length of the wick 100 lying below the insoluble barrier 110 by a wicking action, where the liquid 65 contacts the solid reactant 70. Absorbing substantially all of the liquid reactant 65 upon opening of the openable barrier 75 allows the device to be used in any orientation, since the chemical reactants will stay in contact with one another regardless of the orientation of the device, and the liquid reactant 65 will not get near the liquid 20 to be delivered to the patient.

Figure 11:
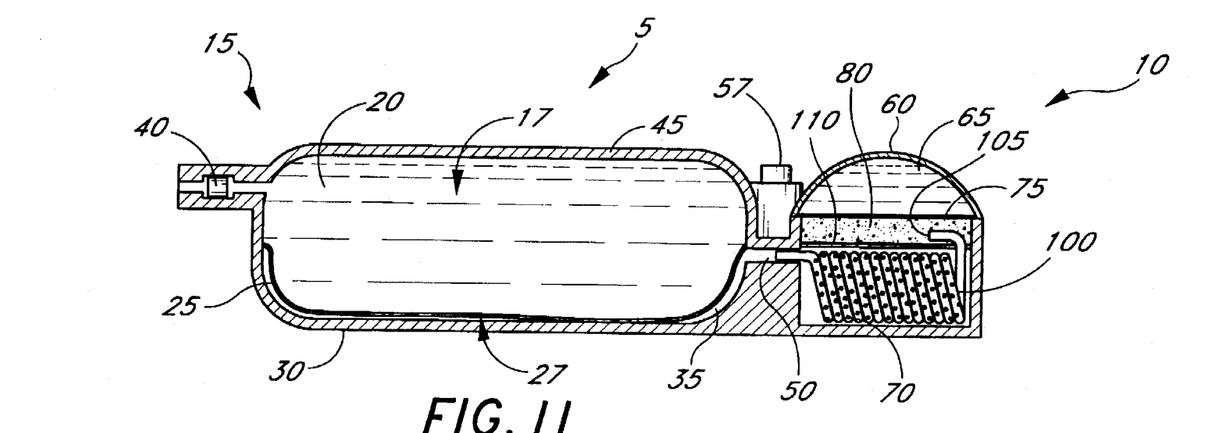
FIG. 11 is a cross-sectional side view of an infusion pump having an alternative embodiment of a fluid delivery system in accordance with the present invention comprising a wick having granules of solid reactant imbedded therein, and a sponge to absorb the liquid reactant in contact with the wick.
Figure 12:
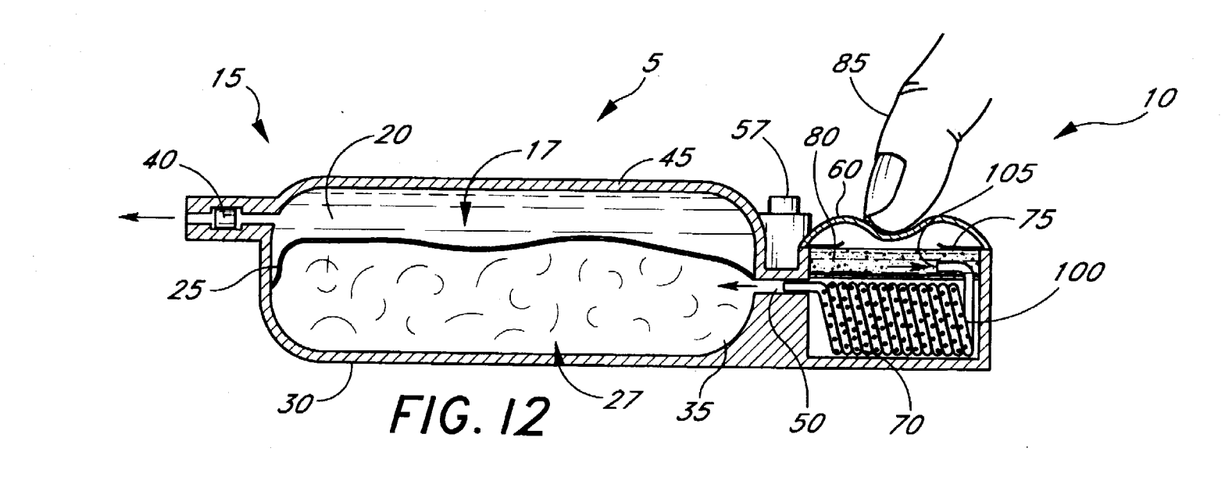
FIG. 12 is a cross-sectional side view of the device of FIG. 11 showing its mode of operation.

In yet another preferred embodiment of the present invention, illustrated in FIGS. 11 and 12, the wick 100 is in contact with an absorbent material, such as a sponge 80, which lies above and is separated from the remainder of the wick by an insoluble barrier 110. The opening of the wick 105 is also separated from the length of the wick 100 by the insoluble barrier 110. The sponge 80 acts to absorb substantially all of the liquid reactant 65, and to keep the liquid reactant 65 in contact with the opening of the wick 105, regardless of the position of the device. The granules of solid reactant 70 are imbedded in the wick 100, and are optionally coated with a time release coating as described above in connection with FIGS. 1 and 2. Pressure on the depressible membrane 60 ruptures the openable barrier 75, bringing the liquid reactant 65 into contact with sponge 80 and with the opening of the wick 105, which lie above and is separated from the remainder of the wick 100 by the barrier 110. The liquid reactant 65 is absorbed by the sponge 80 and enters the opening of the wick 105 and travels along the length of the wick 100 at a predetermined rate which is established by the nature of the wick material. As described above, as the liquid reactant 65 contacts the solid reactant 70, gas is produced by the resulting reaction and travels out of the wick 100 in the direction opposite the flow of the liquid 65, and into the gas expansion reservoir 27. The desired flow rate of fluid from the pump can be achieved by controlling the rate at which the gas is generated and the gas pressure within the device.

Figure 7:
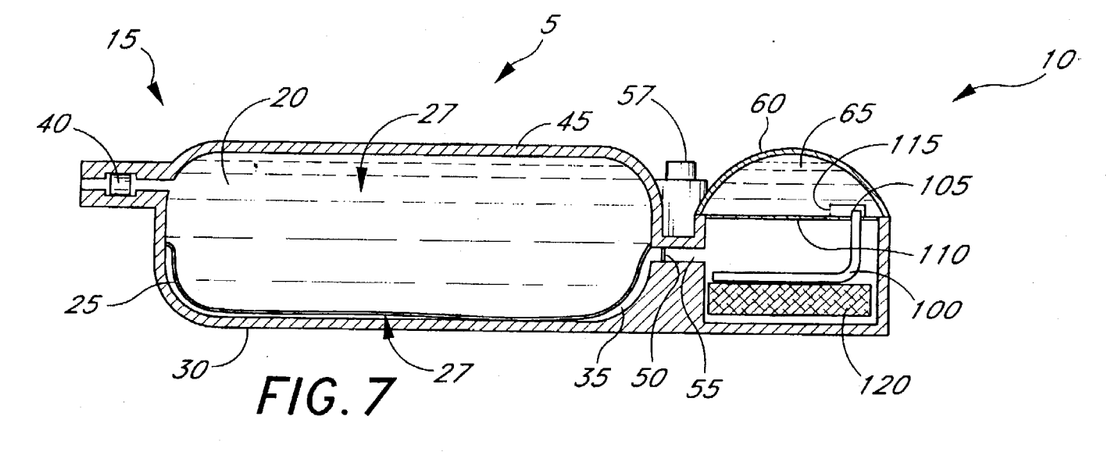
FIG. 7 is a cross-sectional side view of an infusion pump having an alternative embodiment of a fluid delivery system in accordance with the present invention comprising a wick in contact with a tablet of solid reactant.
Figure 8:
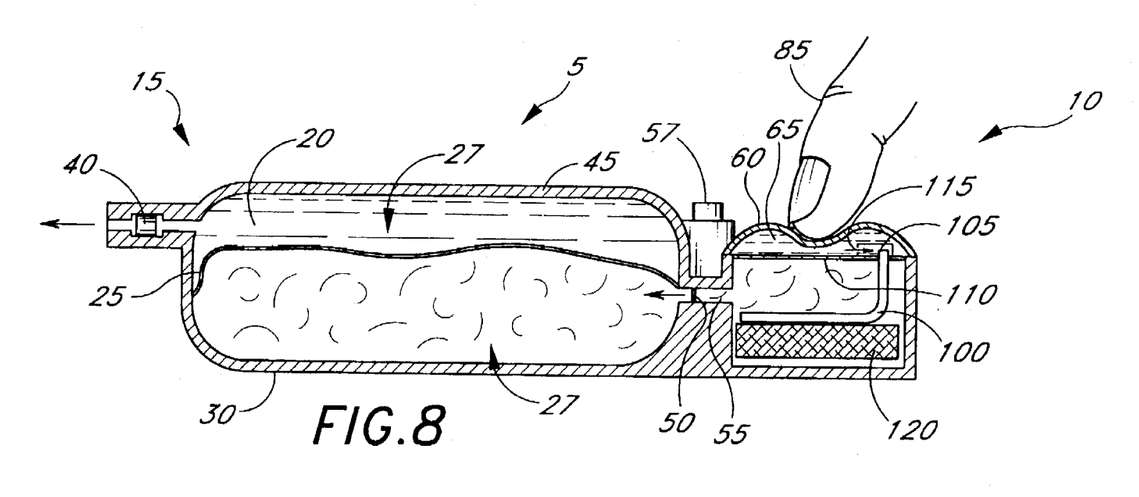
FIG. 8 is a cross-sectional side view of the device of FIG. 7 showing its mode of operation.

In still another preferred embodiment of the present invention, illustrated in FIGS. 7 and 8, the openable barrier comprises a valve 115. Pressure on the depressible membrane 60 forces the liquid reactant 65 through the valve 115 and into contact with the opening of the wick 105, which is separated from the length of the wick 100 by an insoluble barrier 110. The liquid reactant 65 is drawn along the length of the wick 100 by a wicking action. The length of the wick 100 is in contact with the solid reactant, which is in the form of a tablet 120. Preferably, the tablet 120 contains sodium carbonate bound with a filler. As the liquid reactant 65 travels along the length of the wick 100, it contacts the solid reactant 120 and gas is generated. The gas then travels through the hole 50 and channel 55 and into the gas expansion reservoir 27. The length of the wick 100 is preferably sufficient to eventually absorb all the liquid reactant upon opening of the valve 115, allowing operation of the device 5 at any orientation, and preventing the liquid reactant 65 from contacting the liquid 20 to be delivered to the patient.

Attainment of Specific Flow Rates:

In order to tailor an infusion pump having a delivery system in accordance with the present invention to particular applications, it is preferable that a user or designer establish a minimum and maximum of reactants that will be necessary to attain a given flow rate over a given period of time. It will be appreciated that in certain infusion applications it is preferable to have relatively low flow rates, whereas in other applications relatively higher flow rates are desired. Pumps prepared in accordance with the present invention can be prepared to generate flow rates from as low or lower than 2 ml per hour to upwards of 200 ml per hour. Particularly preferred flow rates are about 5, 10, 15, 20, 50, 100, 150, or 200 ml per hour. Therefore, a pump can be prepared with sufficient chemical reactants to allow only a fluid flow rate of 5 or 10 ml per hour. Or, the pumps can be similarly prepared to provide a flow rate of 150 or 200 ml per hour.

To attain a particular flow rate, a flow rate profile should be settled upon. The flow rate profile will govern the choice and design of the porous material and the tablet or solid reactant design, including the use of fillers, delayed reaction coatings, and tablet size and geometry. In connection with consideration of the flow rate profile, the desired start-up speed (i.e., the rate at which the gas generation reaction attains static operating pressure), the length of the delivery that is required and the quantity that is required to be delivered during the time period (i.e., 10 ml/hr for 20 hours versus 20 ml/hr for 10 hours; in each instance requiring delivery of 200 ml but in different time periods), and any additional factors, such as flow rate steps and the like, should be considered.

As an additional consideration, as mentioned above, in order to attain particular flow rates, a calibrated orifice in the fluid reservoir outlet channel can be utilized to attain a particular flow rate under particular reaction conditions.

The specific quantities of reactants necessary to achieve desired flow rates will depend on the particular choice of the reactants and the pressure and/or flow rate profile desired. Such quantities will be determinable empirically by one of ordinary skill in the art. Such experiments can be run as described below:

Reaction Length:

Side-by-side tests can be run with tablets described in connection with FIGS. 7 and 8 having varying quantities of solid and liquid reactants and binders in containers (i.e., erlenmeyer flasks) which are closed after the reaction is initiated with a one-hole stopper having a tube running into individual upside down beakers filled with, and in a pool of, water. The gas generated in the reaction will displace the water from the beaker and the time for the complete reaction can be measured to give the reaction length.

Flow Rate:

Once the reaction length is known for a chosen composition, a general flow rate can be readily determined through measuring the length of time required to displace a given quantity of liquid. For example, a graduated cylinder can be filled with, and placed upside down in a pool of, water and displacement can be measured as described for reaction length.

It is evident from the foregoing that there are many additional embodiments of the present invention which, while not expressly described herein, are within the scope of this invention and may suggest themselves to one of ordinary skill in the art. It is therefore intended that the invention be limited solely by the appended claims.

What is claimed is:

1. An apparatus for delivering a fluid, comprising:
   a first compartment containing said fluid and having a fluid delivery outlet;
   a second compartment in pressure-transferring communication with said first compartment such that gas pressure in said second compartment serves to pressurize said fluid in said first compartment;
   a third compartment initially separately containing a solid and a liquid reactant, wherein said liquid reactant and said solid reactant generate a gas when combined together;
   a wicking material adapted to carry said liquid reactant into contact with said solid reactant, wherein a first portion of said wicking material is in contact with said solid reactant and a second portion is adapted to contact said liquid reactant;
   an openable barrier interposed between said wicking material and said liquid reactant such that upon opening said barrier, said liquid reactant contacts said second portion of wicking material, which in turn carries said liquid reactant into contact with said solid reactant, whereupon a gas is generated, pressurizing said fluid to deliver said fluid out of said outlet.

2. The apparatus of claim 1, wherein said barrier is a valve.

3. The apparatus of claim 1, wherein said barrier is a frangible material.

4. The apparatus of claim 1, further comprising a flexible membrane separating said first compartment from said gas for transferring pressure from said gas to said fluid.

5. The apparatus of claim 1, wherein said first compartment is defined by a first wall comprising said membrane and a second, relatively rigid wall.

6. The apparatus of claim 1, wherein said first compartment is defined by a first wall comprising said membrane and a second, relatively flexible wall.

7. The apparatus of claim 1, wherein said solid reactant is dispersed in said wicking material.

8. The apparatus of claim 1, wherein said solid reactant is in the form of a plurality of solid particles.

9. The apparatus of claim 8, wherein at least some of said solid particles are coated with soluble coating which delays contact between said solid reactant and said liquid reactant.

10. The apparatus of claim 7, wherein said solid reactant is at least partially enclosed by said wicking material.

11. The apparatus of claim 1, wherein said solid reactant is selected from the group consisting of sodium carbonate, sodium bicarbonate, magnesium carbonate, and calcium carbonate.

12. The apparatus of claim 1, wherein said liquid reactant is a solution of an organic acid.

13. The apparatus of claim 11, wherein the organic acid is selected from the group consisting of citric acid and acetic acid.

14. The apparatus of claim 1, wherein said liquid reactant is a solution of sodium bisulfate.

15. The apparatus of claim 1, wherein said apparatus further comprises a relief valve located between said second and third compartments in fluid communication with said gas.

16. An apparatus for the generation of a gas used to deliver fluid, comprising:

a first compartment containing a solid reactant in contact with a porous material;

a second compartment containing a liquid reactant that is reactive with said solid chemical to form a gas;

an openable barrier separating said first compartment from said second compartment such that upon opening said barrier, said liquid reactant contacts said porous material which in turn carries said liquid reactant into contact with said solid reactant, whereupon said gas is generated; and an outlet in said first or second compartment for directing said gas.

17. The apparatus of claim 16, wherein said solid reactant is selected from the group consisting of sodium carbonate, sodium bicarbonate, magnesium carbonate, and calcium carbonate.

18. The apparatus of claim 16, wherein said liquid reactant is a solution of an organic acid.

19. The apparatus of claim 18, wherein the organic acid is selected from the group consisting of citric acid and acetic acid.

20. The apparatus of claim 16, wherein said liquid reactant is a solution of sodium carbonate.

21. The apparatus of claim 16, wherein said porous material is a sponge.

22. The apparatus of claim 16, wherein said porous material is a wick.

23. The apparatus of claim 16, wherein said solid reactant is in the form of a plurality of solid particles.

24. The apparatus of claim 23, wherein at least some of said solid particles are coated with a soluble coating which delays contact between said solid reactant and said liquid reactant.

25. The apparatus of claim 16, wherein said solid reactant is in the form of a tablet.

26. The apparatus of claim 25, wherein said tablet is formed of a plurality of small granules.

27. The apparatus of claim 25, wherein said tablet contains at least one modifier to slow the gas generating reaction between the solid reactant and the liquid reactant.

28. The apparatus of claim 27, wherein said modifier is a binder or filler.

29. The apparatus of claim 16, wherein said outlet further comprises a relief valve.

30. A device for the controlled delivery of fluid, comprising:

a fluid impermeable casing containing the fluid and having an outlet disposed within the casing which allows passage of the fluid out of the casing;

a flexible membrane disposed within the casing and dividing the casing into a liquid reservoir and a gas expansion reservoir;

a gas generating chamber in fluid communication with the gas expansion reservoir;

a solid reactant in contact with a porous material and a liquid reactant, said reactants being initially separately disposed in said gas generating chamber, and being reactive with each other such that they generate gas upon contact; and an openable barrier initially separating said solid and liquid reactants.

31. The device of claim 30, wherein said solid reactant is selected from the group consisting of sodium carbonate, sodium bicarbonate, magnesium carbonate, and calcium carbonate.

32. The device of claim 30, wherein said liquid chemical is a solution of an organic acid or sodium bisulfate.

33. The device of claim 30, wherein said solid reactant is in the form of a plurality of solid particles.

34. The device of claim 33, wherein said particles are coated with a soluble coating which delays contact between the solid reactant and the liquid reactant.

35. The device of claim 30, wherein said porous material is a sponge.

36. The device of claim 30, wherein said porous material is a wick.

37. The device of claim 30, wherein said porous material is sized so as to absorb substantially all of said liquid reactant.

38. The device of claim 30, further comprising a relief valve in fluid communication with said gas generating chamber or said gas expansion reservoir.

39. An apparatus for the generation of carbon dioxide gas used to deliver fluid from a container, comprising:

a first compartment containing said fluid and having a fluid delivery outlet;

a second compartment containing sodium carbonate in contact with a porous material adapted to bring a solution of citric acid into contact with said sodium carbonate whereupon carbon dioxide gas is generated;

a third compartment containing said solution of citric acid;

an openable barrier separating said first compartment from said second compartment; and an outlet for directing said carbon dioxide gas.

40. The apparatus of claim 39, wherein said porous material is a sponge.

41. The apparatus of claim 39, wherein said porous material is a wick.

42. The apparatus of claim 39, wherein said sodium carbonate is in the form of a plurality of solid particles imbedded in said porous material.

43. The apparatus of claim 42 wherein at least some of said particles are coated with a soluble coating which delays contact between said sodium carbonate and said solution of citric acid.

* * * * *